(12) United States Patent
Davies et al.

(10) Patent No.: US 9,352,103 B2
(45) Date of Patent: May 31, 2016

(54) PUSH ROD ACTIVATED MEDICATED MODULE

(75) Inventors: James Alexander Davies, Leamington Spa (GB); Andrew Gordon Wallace, Highleadon (GB); Malcolm Stanley Boyd, Wellesbourne (GB); David Sanders, Warwick (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 943 days.

(21) Appl. No.: 13/576,632

(22) PCT Filed: Feb. 1, 2011

(86) PCT No.: PCT/EP2011/051410
§ 371 (c)(1),
(2), (4) Date: Dec. 17, 2012

(87) PCT Pub. No.: WO2011/095489
PCT Pub. Date: Aug. 11, 2011

(65) Prior Publication Data
US 2013/0090604 A1 Apr. 11, 2013

Related U.S. Application Data

(60) Provisional application No. 61/301,693, filed on Feb. 5, 2010.

(30) Foreign Application Priority Data

Apr. 23, 2010 (EP) .................................... 10160854

(51) Int. Cl.
*A61M 5/32* (2006.01)
*A61M 5/24* (2006.01)
(Continued)

(52) U.S. Cl.
CPC ........... *A61M 5/3245* (2013.01); *A61M 5/2448* (2013.01); *A61M 5/284* (2013.01);
(Continued)

(58) Field of Classification Search
CPC . A61M 3/005; A61M 5/2066; A61M 5/2448; A61M 5/284; A61M 5/3243; A61M 5/3245; A61M 5/3294; A61M 2005/3247; A61M 2005/3267; A61M 5/31596; A61M 2005/2451
USPC ..................... 604/82–92, 198, 240–243, 416; 206/438, 364–367
See application file for complete search history.

(56) References Cited

U.S. PATENT DOCUMENTS 5,242,401 A 9/1993 Colsky
6,562,002 B1 5/2003 Taylor
(Continued)

FOREIGN PATENT DOCUMENTS

JP S49-77487 7/1974
JP 2005-510308 4/2005
(Continued)

OTHER PUBLICATIONS

Japanese Office Action for JP Application No. 2012-551600, mailed Nov. 11, 2014.
International Search Report and Written Opinion for Int. App. No. PCT/EP2011/051410, mailed May 30, 2011.

*Primary Examiner* — Edelmira Bosques
*Assistant Examiner* — Leah Swanson
(74) *Attorney, Agent, or Firm* — McDonnell Boehnen Hulbert & Berghoff LLP

(57) ABSTRACT

A medicated module for an injection system to co-deliver at least two medicaments is disclosed. The drug delivery device includes a push rod operably connected to a dose dial button. The medicated module includes a housing having a connector configured for attachment to the drug delivery device, and the housing is configured to receive a portion of the push rod when the medicated module is attached to the drug delivery device. The medicated module further includes a reservoir in the housing comprising a single dose of a medicament and a needle guard operably connected to the housing and configured to move in an axial direction during application to an injection site. Still further, the medicated module includes a sleeve in the housing configured to move axially in the housing and a locking collar in the housing configured to move axially and rotationally in the housing.

16 Claims, 9 Drawing Sheets

(51) Int. Cl.
*A61M 5/28* (2006.01)
*A61M 5/31* (2006.01)
*A61M 5/315* (2006.01)
*A61M 5/34* (2006.01)
*A61M 5/50* (2006.01)
*A61M 5/178* (2006.01)

(52) U.S. Cl.
CPC ............ *A61M 5/326* (2013.01); *A61M 5/2466* (2013.01); *A61M 5/288* (2013.01); *A61M 5/3146* (2013.01); *A61M 5/3155* (2013.01); *A61M 5/31525* (2013.01); *A61M 5/3294* (2013.01); *A61M 5/3297* (2013.01); *A61M 5/347* (2013.01); *A61M 5/5086* (2013.01); *A61M 2005/1787* (2013.01); *A61M 2005/3247* (2013.01); *A61M 2005/3267* (2013.01); *A61M 2205/583* (2013.01)

(56) References Cited

U.S. PATENT DOCUMENTS

| | | |
|---|---|---|
| 2005/0065476 A1 | 3/2005 | Jensen et al. |
| 2006/0276755 A1 | 12/2006 | Sullivan et al. |
| 2009/0018506 A1 | 1/2009 | Daily et al. |
| 2012/0136316 A1* | 5/2012 | Davies .................. A61M 5/284 604/191 |
| 2012/0226238 A1* | 9/2012 | Davies .................. A61M 5/326 604/191 |

FOREIGN PATENT DOCUMENTS

| | | |
|---|---|---|
| WO | 01/76665 | 10/2001 |
| WO | 2007/026163 | 3/2007 |

\* cited by examiner

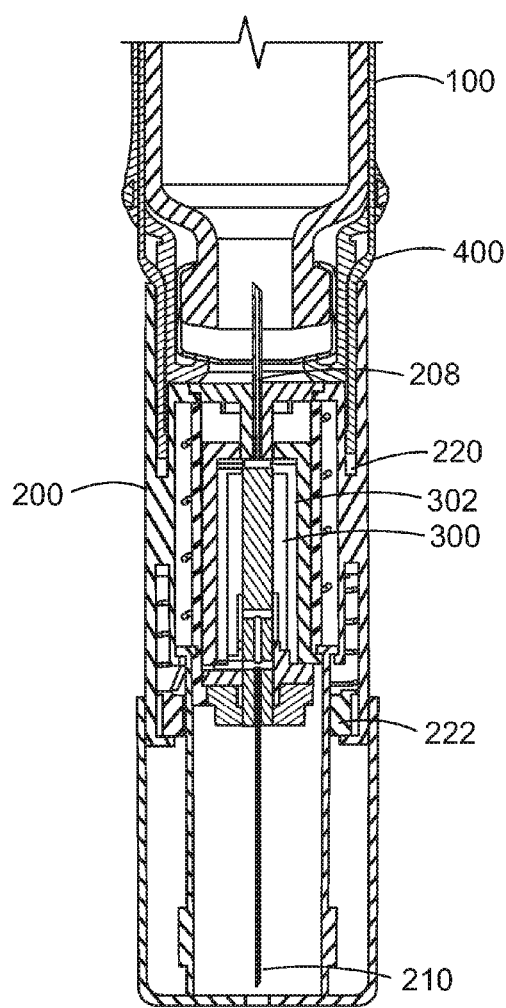
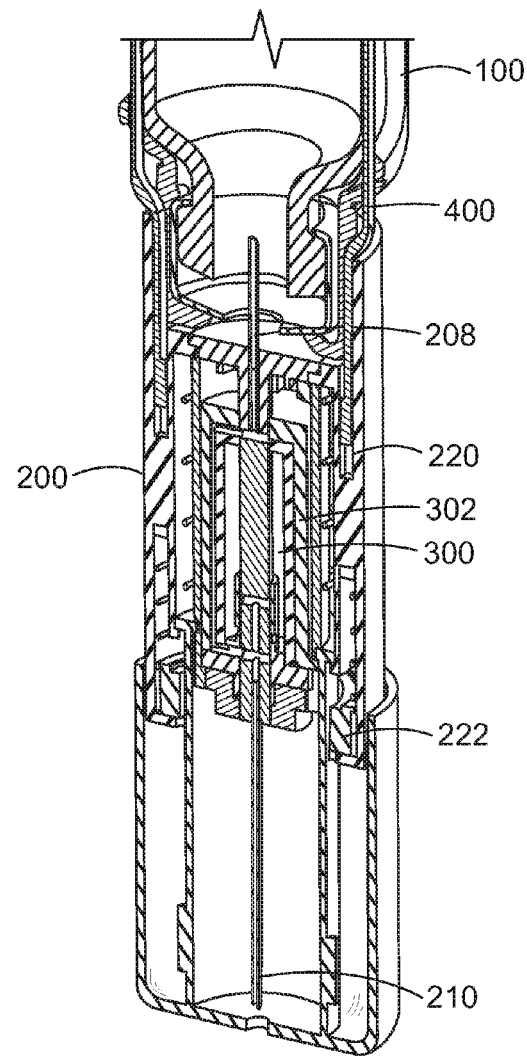
FIG. 5
FIG. 6

PUSH ROD ACTIVATED MEDICATED MODULE

CROSS REFERENCE TO RELATED APPLICATIONS

The present application is a U.S. National Phase Application pursuant to 35 U.S.C. §371 of International Application No. PCT/EP2011/051410 filed Feb. 1, 2011, which claims priority to U.S. Provisional Patent Application No. 61/301,693 filed on Feb. 5, 2010 and European Patent Application No. 10160854.5 filed Apr. 23, 2010. The entire disclosure contents of these applications are herewith incorporated by reference into the present application.

FIELD OF INVENTION

Specific embodiments of the present disclosure relate to medical devices and methods of delivering at least two drug agents from separate reservoirs using devices having only a single dose setting mechanism and a single dispense interface. A single delivery procedure initiated by the user may cause a non-user settable dose of a second drug agent and a variable set dose of a first drug agent to be delivered to the patient. The drug agents may be available in two or more reservoirs, containers or packages, each containing independent (single drug compound) or pre-mixed (co-formulated multiple drug compounds) drug agents. Specifically, embodiments of this disclosure concern a medicated module that has a needle guard that locks out after a predefined number of doses is delivered. Thereby, unintended reuse of the medicated module may be prevented.

BACKGROUND

Certain disease states require treatment using one or more different medicaments. Some drug compounds need to be delivered in a specific relationship with each other in order to deliver the optimum therapeutic dose. The presently proposed devices and methods may be of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two active medicaments or "agents" simultaneously. The two active agents may interact with each other during the long-term, shelf life storage of the formulation. Therefore, it is advantageous to store the active components separately and combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example one or more active agents may require a titration period to gradually introduce a patient up to a "maintenance" dose. A further example would be if one active agent requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more that one drug delivery system or make the necessary accurate calculation of the required dose combination. This is especially true for users with dexterity or computational difficulties. In some circumstances it may be also necessary to perform a priming procedure of the device and/or needle cannulae before dispensing the medicaments. Likewise, in some situations, it may be necessary to bypass one drug compound and to dispense only a single medicament from a separate reservoir.

Accordingly, there exists a need to provide devices and methods for the delivery of two or more medicaments in a single injection or delivery step that is simple for the user to perform. Specific embodiments of the presently proposed devices and methods overcome the above-mentioned problems by providing separate storage containers for two or more active drug agents that are then only combined and/or delivered to the patient during a single delivery procedure. Setting a dose of one medicament may automatically fix or determine the dose of the second medicament (i.e. non-user settable). The proposed devices and methods may also give the opportunity for varying the quantity of one or both medicaments. For example, one fluid quantity may be varied by changing the properties of the injection device (e.g. dialing a user variable dose or changing the device's "fixed" dose). The second fluid quantity may be changed by manufacturing a variety of secondary drug containing packages with each variant containing a different volume and/or concentration of the second active agent. The user or healthcare professional would then select the most appropriate secondary package or series or combination of series of different packages for a particular treatment regime.

One problem to be solved by the present invention is to provide a medicated module, a needle assembly, a drug delivery system and a method of dispensing a medicament where the administration of a medicament is improved.

SUMMARY

The disclosed medicated module and drug delivery device may allow complex combinations of multiple drug compounds within a single drug delivery system. According to specific embodiments, a user may be allowed to set and dispense a multi-drug compound device through one single dose setting mechanism and a single dispense interface. This single dose setter may control the mechanism of the device such that a predefined combination of the individual drug compounds is delivered when a single dose of one of the medicaments is set and dispensed through the single dispense interface.

By defining the therapeutic relationship between the individual drug compounds, the proposed delivery device and delivery methods may help ensure that a patient/user receives the optimum therapeutic combination dose from a multi-drug compound device without the inherent risks associated with multiple inputs where the user has to calculate and set the correct dose combination every time he uses the device. The medicaments can be fluids, defined herein as liquids or gases or powders that are capable of flowing and that change shape at a steady rate when acted upon by a force tending to change its shape. Alternatively, one or both of the medicaments may be a solid that is carried, solubilized or otherwise dispensed with another fluid medicament.

Specific embodiments of the disclosed medicated module and drug delivery device may be of particular benefit to users with dexterity or computational difficulties as the single input and associated predefined therapeutic profile removes the need for them to calculate their prescribed dose every time they use the device and the single input allows considerably easier setting and dispensing of the combined compounds.

In a preferred embodiment a master drug compound, such as insulin, contained within a multiple dose, user selectable device could be used with a single use, user replaceable, module that may contain a single dose of a secondary medicament and the single dispense interface. When connected to the primary device, the secondary compound may be activated/delivered on dispense of the primary compound. Although the present disclosure specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used.

In the following, the term "insulin" shall mean insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29Lys may be replaced by Pro; Ala (B26) human insulin; Des(B28-B30) human insulin; Des (B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28 ProB29 human insulin; B28-N-palmitoyl-LysB28 ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

According to one aspect, a medicated module is provided. The medicated module may be attachable to a drug delivery device. The drug delivery device may comprise a primary reservoir for retaining a first medicament. The medicated module may comprise a second medicament. Preferably, the second medicament is placed in the medicated module before the medicated module is attached to the drug delivery device. The drug delivery device, in particular the primary reservoir, is preferably filled with first medicament before the module is attached to the device. The medicated module may be particularly suited for an injection device, for example a pen type injection device. The device may be suitable to set and dispense a dose of the first medicament held in the primary reservoir before the medicated module is attached to the device or after the medicated module was removed from the device. Accordingly, the device may be suitable to form a stand-alone device, configured to operate also in absence of the medicated module, for example. For this purpose, a needle cannula may be, preferably removably, attachable to the distal end of the device.

As examples, the reservoir in the medicated module may contain a liquid medicament. The medicament may be a GLP-1 or a premix of insulin and a GLP-1. The drug delivery device may comprise a dose button. The dose button can be any triggering mechanism that causes a dose of the first medicament to be dispensed from the device. The dose button may be a dose dial button. The drug delivery device may comprise a device coupling member. The device coupling member may be operably connected to the dose button. The device coupling member may be axially movable when the dose button is activated, in particular when the dose button is activated for delivering a dose. Here, for example the dose button may be fully depressed by a user of the drug delivery device. Movement of the dose button may then be transferred to movement of the device coupling member in the distal direction by mechanical cooperation of the device coupling member and the dose button In particular, the device coupling member may be activated only when the dose button is moved distally. The device coupling member may operably connect the medicated module to an activation of the dose button. In particular, the coupling member may comprise a push rod operably connected to a dose button, which is described later on in more detail. The push rod may be axially moveable when the dose button is fully depressed by a user of the drug delivery device.

The medicated module may comprise a housing. The housing may comprise a connector configured for attachment to the drug delivery device. The housing may be configured to receive a portion of the device coupling member, for example a push rod, when the medicated module is attached to the drug delivery device. The medicated module may further include a reservoir in the housing comprising at least one dose of a medicament. The reservoir may include a single dose of a medicament, for example a second medicament. The medicated module may be a medicated needle. The medicated module may comprise a first or proximal needle cannula. The medicated module may comprise a second or distal needle cannula. The reservoir of the module may be arranged in the axial direction between the first and the second needle cannula. The needle cannulae may be adapted and arranged for establishing fluid communication with the reservoir of the module. The distal end of the second needle cannula may be configured for being applied to an injection site. The proximal end of the second needle cannula may be configured for piercing the reservoir of the module, in particular a seal or septum arranged at the distal end of the secondary reservoir. The distal end of the first needle cannula may be configured for piercing the reservoir of the module, in particular a seal or septum arranged at the proximal end of the secondary reservoir. The proximal end of the first needle cannula may be configured for piercing the primary reservoir, in particular a seal or septum arranged at the distal end of the primary reservoir. The medicated module may comprise a needle guard for providing protection against at least one of the needle cannulae arranged in a portion of the medicated module. The needle guard may be a needle guard assembly. The needle guard may be configured to move in axial direction during application to an injection site. The needle guard may be operably connected to a housing of the medicated module.

Still further, the medicated module may comprise locking means for disabling axial movement of the needle guard. The locking means may be configured to be operably connected to an activation of the dose button of a drug delivery device and operably connected to an axial movement of the needle guard. The locking means may be further configured to disable the needle guard from moving axially only after a predefined number of dose delivery operations, wherein a dose delivery operation comprises the steps of moving the needle guard in axial direction and activating the dose button for delivering a dose. The locking means may comprise a module coupling member being configured to be engageable with a device coupling member of a drug delivery device. The device coupling member may be operably connected to the dose button and, in particular, may operably connect the locking mechanism to an activation of the dose button. The module coupling member may be configured to be axially movable. The module coupling member may comprise or may be designed as a sleeve, which may be located in a housing of the medicated module, configured to move axially. Furthermore, the locking mechanism may comprise a rotating member configured to move rotationally. In particular, the rotating member may be configured such that it carries out a defined rotational movement after each dose delivery operation, thereby counting the number of delivered doses. The rotating member may be configured to move both axially and rotationally. The rotating member may be designed as or may comprise a locking collar. The rotating member may be caused to rotate by the module coupling member after a given dose has been delivered. In particular, the module coupling member may comprise a first slanted feature and the rotating member may comprise a second slanted feature. When a given dose has been delivered, the first slanted feature and the second slanted feature may interact to force the rotating member to rotate, so as to facilitate counting the given dose as delivered. Furthermore, the medicated module may comprise a first spring, wherein the first spring is operably connected to the needle guard. The first spring may force the needle guard in an axial direction, in particular in a distal direction when the needle guard is retracted in a proximal direction and removed from an injection site. The medicated module may further comprise a second spring operably connected to the rotating member, for example a locking collar. The second spring may force the rotating member in an axial direction so as to facilitate counting the given dose as delivered. In one embodiment, during delivery of the dose, the needle guard is in a retracted position and the device coupling member is activated, for example a push rod of the device coupling member may be in a depressed position. The locking means may be configured such that it is activated by the needle guard being in a retracted position and the activation of the coupling member due to an activation of the dose button. In particular, the locking means may be configured to count the number of such dose delivery operations. In particular, the locking means may be configured such that only an activation of the dose button in a retracted position of the needle guard is counted as a dose delivery operation. The locking mechanism and, in particular, a rotating member of the locking mechanism may be further configured to prevent the needle guard assembly from moving axially after a predefined number of doses has been delivered via the medicated module. Preferably, the needle guard is axially movable until the predefined number of dose delivery operations has been carried out. In particular, the needle guard may be allowed to move axially to a retracted position after the dose button and, thereby, the device coupling member has been activated provided that the needle guard was not in the retracted position when the dose button was activated. Moreover, the needle guard may be allowed to move axially several times to a retracted position before the dose button has been activated to deliver a dose. In order to achieve locking of the needle guard, the needle guard may comprise a locking feature for disabling axial movement of the needle guard, wherein the rotating member engages with the locking feature after a predefined number of doses has been delivered. Thereby, the needle guard may be locked to the rotating member. In particular, the locking mechanism may be configured such that the needle guard will lock in a covering or fully extended distal position after a dose is delivered. This may prevent unintended reuse of the module.

According to specific embodiments of the medicated module and the drug delivery device, with a single activation of the dose button, when the needle guard is retracted, the medicament from the primary reservoir and the second medicament from the medicated module can be expelled through an output needle in the module. Upon completion of the delivery procedure, substantially all of the second medicament may have been expelled as well as the selected dose of the first medicament through the single dispense interface. By "substantially all" we mean that at least about 80% of the second medicament is expelled from the drug delivery device, preferably at least about 90% is expelled. Additionally, if more of the primary medicament needs to be injected, another dose can be set and injected before the needle guard locks out.

According to specific embodiments, the medicated module may comprise first and second needle cannulae, where the first needle cannula may be mounted in a proximal end of the module and the second needle cannula may be mounted in a distal end of the module. The two needle cannulae may be not in fluid communication with the medicament in the reservoir of the module when the needle guard is fully extended in a distal direction. The two needle cannulae may be in fluid communication with the medicament when the needle guard is retracted in a proximal direction. The medicated module may comprise a bypass for example a bypass channel, bypassing the medicament in the reservoir. The needle cannulae may be in fluid communication with the bypass when the needle guard is fully extended in a distal direction.

In one embodiment, for example in an embodiment as shown in FIG. 2, the locking mechanism only counts a single needle guard retraction before locking out. Here, the needle guard is locked after a subsequent extension in the distal direction. In particular, an activation of the dose button may result in pressing the device coupling member on the module coupling member and thereby, the module coupling member on the rotating member. As an example, a dose delivery operation may result in pressing a sleeve of the coupling member onto a locking collar of the rotating member. Thereby, the rotating member, for example the locking collar, may be caused to rotate such that when the needle guard extends again, the needle guard finishes, in a position that is locked out. However, according to further embodiments, the locking mechanism can be configured to count multiple doses before locking out. As an example, the predefined number of doses may be in a range from one dose to four doses. To allow predefined multiple doses before lock out, the locking mechanism may be configured such that the rotating member, for example a locking collar, may carry out a defined rotational movement and in particular, a predefined amount of rotational movement after each dose delivery operation. Thereby, the locking means counts the number of delivered doses and locks out after a predefined number of doses, for example after multiple doses, have been delivered. The module coupling member, for example a sleeve, or the rotating member, for example a locking collar, may have additional teeth designed to gradually rotate the rotating member a known distance each time the needle guard is retracted and extended and the dose button is activated. After a defined number of increments (the required dose count) the needle guard would then lock in the extended position. For example: in order to count two doses before locking out, the locking collar and/or sleeve could have two teeth; in order to count three doses, the locking collar and/or sleeve could have three teeth, and so forth.

According to a first specific embodiment, a medicated module attachable to a drug delivery device is provided, wherein the drug delivery device comprises a primary reservoir for retaining a first medicament and wherein the medicated module comprises a second medicament. The medicated module further comprises a reservoir for retaining the second medicament and a needle guard to provide protection against at least one needle arranged in a portion of the medicated module and configured to move in an axial direction during application to an injection site. The medicated module further comprises locking means for disabling axial movement of the needle guard, the locking means being configured to be operably connected to an activation of a dose button of the drug delivery device and to an axial movement of the needle guard. Moreover, the locking means are further configured to disable the needle guard from moving axially only after a predefined number of dose delivery operations, wherein a dose delivery operation comprises the steps of moving the needle guard in axial direction and activating the dose button for delivering a dose.

According to a further specific embodiment, a medicated module attachable to a drug delivery device is provided. The drug delivery device includes a push rod operably connected to a dose dial button, wherein the push rod is axially moveable when the dose dial button is depressed by a user of the drug delivery device. The medicated module comprises a housing having a connector configured for attachment to the drug delivery device, wherein the housing is configured to receive a portion of the push rod when the medicated module is attached to the drug delivery device. Further, the medicated module comprises a reservoir in the housing comprising a single dose of a medicament. Moreover, the medicated module comprises a needle guard assembly operably connected to the housing and configured to move in an axial direction during application to an injection site, a sleeve in the housing configured to move axially in the housing and a locking collar in the housing configured to move axially and rotationally in the housing, wherein, during delivery of the dose, the needle guard is in a retracted position and the push rod is in a depressed position, and wherein the locking collar is further configured to prevent the needle guard assembly from moving axially after a predefined number of doses are delivered via the medicated module.

According to a further aspect, a needle guard assembly for a drug delivery device is provided. The needle guard assembly comprises a needle guard and locking means as described above. In particular, the locking means may be configured to disable the needle guard from moving axially only after a predefined number of dose delivery operations have been carried out. The needle guard assembly may comprise a reservoir for retaining a medicament or may be free from such a reservoir. The operation of the needle guard and locking means in the needle guard assembly may be similar or identical to the operations as described above in connection with the medicated module.

According to a further aspect, a drug delivery system comprising the medicated module or comprising the needle guard assembly as described above is provided. In case that the drug delivery system comprises the medicated module it may comprise a primary reservoir of medicament containing at least one drug agent, where the medicated module is configured for fluid communication with the primary reservoir. As examples, the primary reservoir or the secondary reservoir or both reservoirs may contain a liquid medicament. The primary reservoir may contain insulin. The secondary reservoir may comprise a GLP-1 or a premix of a GLP-1 and insulin. The drug delivery device may be configured to deliver two or more medicaments. The drug delivery device comprises a dose button operably connected to the locking means of the medicated module and a device coupling member operably connecting the dose button to the locking means. The drug delivery system may be operable through a single dose setter and a single dispense interface. It may comprise a housing containing a single dose setter operably connected to the primary reservoir of medicament and a dose button operably connected to the primary reservoir of medicament. The device coupling member may be designed as a push rod operably connected to the dose button, wherein the push rod is axially movable when the dose button is depressed by a user of the drug delivery system.

For delivering a dose, the drug delivery system described above may be operated as follows:
(i) the given dose is selected, upon which the device coupling member and module coupling member move in a first axial direction,
(ii) the needle guard is retracted in the first axial direction, thereby forcing the rotating member to move axially in the first direction,
(iii) the device coupling member thereafter moves in a second axial direction and forces the module coupling member to move in the second axial direction, wherein the second direction is substantially opposite the first direction, and
(iv) the module coupling member interacts with the rotating member and forces the rotating member to rotate circumferentially,
(v) as the needle guard extends in a second axial direction substantially opposite to the first axial direction, it allows the rotating member to move axially in the second direction and rotate circumferentially, so as to count the given dose as delivered.

According to still a further aspect, a method of dispensing a medicament is disclosed. The method may be used for testing purposes and may not comprise a treatment of the human or animal body by surgery or therapy. The method comprises the steps of:
a. attaching a medicated module as described above to a drug delivery device, wherein the drug delivery device comprises a dose button and a device coupling member operably connected to the dose button;
b. setting a dose of medicament on the drug delivery device such that the device coupling member is moved proximally; and c. activating the dose button to administer the set dose causing the device coupling member to move axially, thereby activating a rotating member disposed in the medicated module, wherein the activation of the rotating member prevents a needle guard in the medicated module from moving axially after a predefined number of doses is delivered.

One aspect relates to a method for testing a drug delivery system, the method comprising the steps of:
A) Providing the previously described medicated module. The reservoir of the module may be filled with a dose of the second medicament.
B) Attaching the medicated module to a drug delivery device. The drug delivery device may comprise a dose button, a primary reservoir of medicament, and a device coupling member operably connected to the dose button. The primary reservoir of the drug delivery device may be, at least party, filled with medicament before the module is attached to the device. Preferably, the primary reservoir contains a plurality of doses of medicament.
C) Setting a dose of medicament on the drug delivery device such that the device coupling member is moved proximally.
D) Activating the dose button to perform a priming operation such that the medicament is forced in the distal direction from the primary reservoir of the drug delivery device. When activating the dose button, the device coupling member may be moved distally. The medicament may be forced through the proximal needle. The medicament may then be forced around the reservoir of the medicated module and through the needle arranged at the distal end of the reservoir.

Furthermore, the method may comprise the steps of:
E) Moving the needle guard of the medicated module in the proximal direction. Thereby, the module coupling member may be moved in the proximal direction by mechanical cooperation of the needle guard and the module coupling member.
F) Setting a further, preferably variable, dose of medicament on the drug delivery device such that the device coupling member is moved proximally.
G) Activating the dose button to move the coupling member distally. Thereby, the module coupling member may be distally by mechanical cooperation with the device coupling member. A rotating member disposed in the medicated module may thereby be activated by mechanical cooperation of the module coupling member and the rotation member. The activation of the rotating member may be configured to prevent the needle guard in the medicated module from moving axially by mechanical cooperation of the rotating member and the needle guard after a predefined number of doses was delivered.

The device coupling member may be a push rod. The push rod may extend axially along the housing of the device, in particular along an inner surface of the housing. The push rod, in particular a distal end section of the push rod, may be configured to protrude from the distal end of the housing. During attachment of the medicated module, the distal end of the push rod may be disposed in a housing of the medicated module. In particular, the distal end section of the push rod may protrude into the proximal end section of the medicated module, such that mechanical cooperation of the push rod and the module coupling member is enabled. A proximal end of the push rod may extend over the proximal end of the housing of the drug delivery device. Accordingly, when the dose button is activated, i.e. moved distally, the dose button may mechanically cooperate with the device coupling member such that the device coupling member is moved in the distal direction. Accordingly, movement of the dose button in the distal direction is transferred into movement of the device coupling member in the distal direction. The rotating member may be configured as a locking collar and may be disposed in a housing of the medicated module. Instead of attaching a medicated module to the device, the method may comprise the step of attaching a needle guard assembly as described above to the device. In this case, further operations steps of the method may be identical or similar to the operation steps as described above.

The medicated module can be designed for use with any drug delivery device with an appropriate compatible interface. However, it may be preferable to design the module in such a way as to limit its use to one exclusive primary drug delivery device (or family of devices) through employment of exclusive, dedicated or coded features to prevent attachment of a non-appropriate medicated module to a non-matching device. In some situations it may be beneficial to ensure that the medicated module is exclusive to one drug delivery device while also permitting the attachment of a standard drug dispense interface to the device. This would allow the user to deliver a combined therapy when the module is attached, but would also allow delivery of the primary compound independently through a standard drug dispense interface in situations, such as, but not limited to, dose splitting or top-up of the primary compound.

A particular benefit is that the proposed medicated module makes it possible to tailor dose regimes when required, especially where a titration period may be required for a particular drug. The medicated module could be supplied in a number of titration levels with obvious differentiation features such as, but not limited to, aesthetic design of features or graphics, numbering, tactile features, audible differentiation, smell differentiation etc, so that a patient could be instructed to use the supplied medicated module in a specific order to facilitate titration. Alternatively, a prescribing physician may provide the patient with a number of "level one" titration medicated modules and then when these were finished or exhausted, the physician could then prescribe the next level. One key advantage of this titration program is that the primary device remains constant throughout.

In a preferred embodiment, the primary drug delivery device is used more than once and therefore is a multi-use device, however, the drug delivery device may also be a single use disposable device. Such a device may or may not have a replaceable reservoir of the primary drug compound. It is also possible to have a suite of different medicated modules for various conditions that could be prescribed as one-off extra medication to patients already using a standard drug delivery device. Should the patient attempt to reuse a previously used medicated module, this module may comprise a locking needle guard that is activated after a user delivers a dose from the medicated module. Other means of alerting the user may include some (or all) of the following:

Physical prevention of medicated module re-attachment to the primary drug deliver device once the module has been used and removed.
Physical/hydraulic prevention of subsequent liquid flow through the drug dispense interface once it has been used.
Physical locking of the dose setter and/or dose button of the primary drug delivery device.
Visual warnings (e.g. change in color and/or warning text/indicia within an indication window on the module once insertion and/or fluid flow has occurred).

Tactile feedback (presence or absence of tactile features on the outer surface of the module hub following use).

A further proposed feature is that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant or who have computational or dexterity difficulties.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which:

FIG. 5 illustrates a cross-sectional view of the embodiment of FIG. 2 where the medicated module is attached to a drug delivery device;

FIG. 6 illustrates a perspective, cross-sectional view of the embodiment of FIG. 2 where the medicated module is attached to a drug delivery device;

DETAILED DESCRIPTION

Specific embodiments of the disclosed medicated module and drug delivery system enable administering a fixed predetermined dose of a secondary drug compound (medicament) and a variable dose of a primary or first drug compound through a single output or drug dispense interface. Setting the dose of the primary medicament by the user may be independent of a single dose of the second medicament, which is preferably contained in a reservoir in a medicated module that is attachable to a drug delivery device. a1

Figure 1:
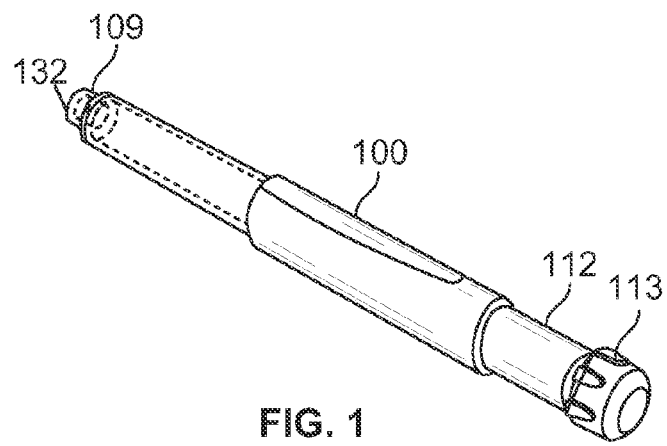
FIG. 1 illustrates a perspective view of one possible drug delivery device that can be used with a medicated module.

In a preferred embodiment the drug dispense interface is a needle cannula (hollow needle). FIG. 1 illustrates one example of a drug delivery device 100 to which a medicated module 200 (see FIGS. 2-15) can be attached to the connection means 109 of distal end 132. Each medicated module 200 is preferably self-contained and provided as a sealed and sterile disposable that has an attachment means compatible to the connection means 109 at the distal end 132 of device 100. Although not shown, the medicated module 200 could be supplied by a manufacturer contained in a protective and sterile container, where the user would peel or rip open a seal or the container itself to gain access to the sterile medicated module 200. In some instances it might be desirable to provide two or more seals for each end of the medicated module 200.

Drug delivery device 100 preferably contains a first (or primary) medicament. The embodiments shown in the figures have the benefit of the second medicament 300 as a single dose being contained entirely within annular reservoir 302, hence minimizing the risk of material incompatibility between the second medicament and the materials used in the construction of the medicated module 200, specifically central core 304 or any of the other parts used in the construction of the module 200.

To minimize the residual volume of the second medicament, caused by recirculation and/or stagnant zones that might remain in reservoir 302 at the end of the dispense operation, it is preferable to have the reservoir 302 configured or designed to maximize the amount of medicament dispensed. A possibly preferred shape is the annulus as shown in the figures.

Figure 2:
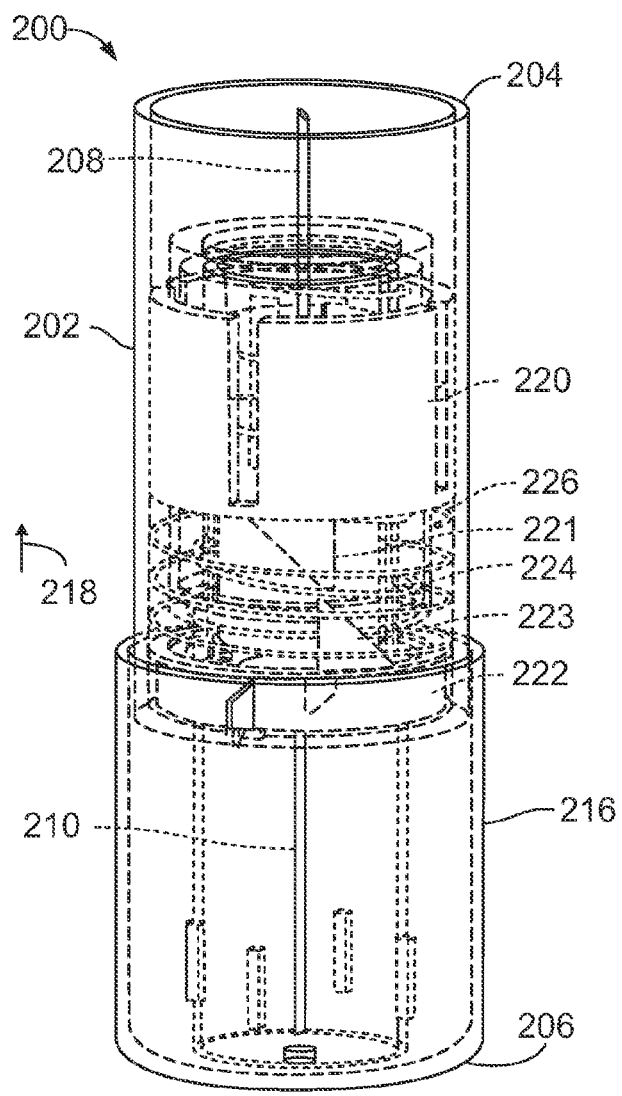
FIG. 2 illustrates a perspective view of an exemplary medicated module.
Figure 3:
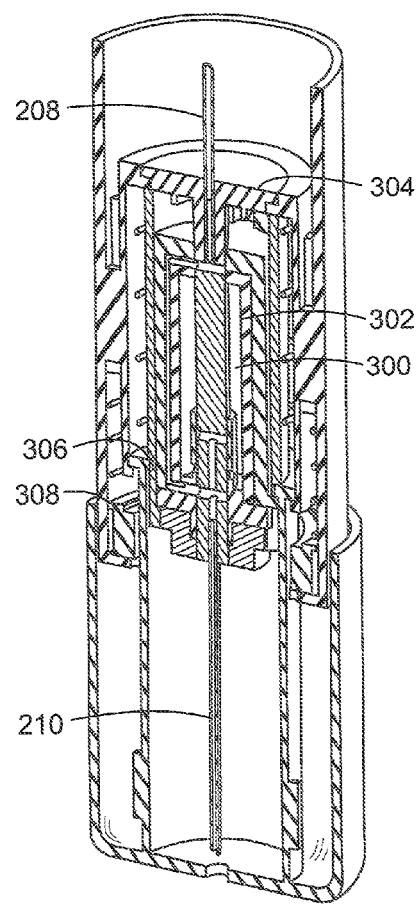
FIG. 3 illustrates a perspective, cross-sectional view of an exemplary medicated module.

Referring to the embodiment shown in FIGS. 2-15, the medicated module 200 and operation of medicated module 200 are described in detail. FIG. 2 illustrates a preferred arrangement of medicated module 200 that is attachable to a drug delivery device, such as drug delivery device 100. Medicated module 200 includes a housing 202 that has a proximal end 204 and a distal end 206. The proximal end 204 has an attachment or connection means (not shown) that is configured for attachment to the drug delivery device 100. Any known attachment means can be used to attach the medicated module 200 to the chosen drug delivery device 100, including all types of permanent and non-permanent connection means, such as threads, snap locks, snap fits, luer locks, bayonet, snap rings, keyed slots, and combinations of such connections. For instance, the attachment means may be a thread that would engage like threads of the distal end 132 of drug delivery device 100.

The medicated module 200 has a first needle cannula 208 that is mounted or fixed in the proximal end 204 of the module 200 and a second needle cannula 210 that is mounted or fixed in the distal end 206 of the module 200. The housing 202 also contains a reservoir 302 located axially between the first and second needles 208, 210 and this reservoir 302 contains a second medicament 300.

A needle guard assembly 216 is positioned in housing 202 and this needle guard assembly 216 is configured to move in an axial direction (defined by arrow 218) during application to an injection site. Preferably, needle guard assembly 216 is tubular-shaped and in a relaxed (or extended) position, as illustrated in FIG. 2, substantially conceals second needle 210. While substantially concealing the second needle, the needle guard 216 also helps to prevent inadvertent needle sticks.

The medicated module 200 further includes a sleeve 220 and a locking collar 222 disposed in the housing 202. The sleeve 220 includes at least one slanted feature 221 and the locking collar 222 includes a complimentary number of slanted feature(s) 223. Additional slanted features on the locking collar 222 and/or sleeve 220 could be used to allow the user to make a predetermined number of injections. Preferably, these slanted features are triangle-shaped features and may be referred to as "teeth". In should be understood, however, that other shaped features are possible as well.

The medicated module 200 also includes a first spring 224 and a second spring 226. First spring 224 is operably connected to proximal end 306 of the needle guard assembly 216, and second spring 226 is operably connected to a proximal end 308 of the locking collar 222. After both springs 224, 226 are compressed, for example, when needle guard assembly 216 moves upward in an axial direction and when locking collar 222 moves upward in an axial direction 218, the springs 224, 226 may supply a force to move the needle guard 216 and the locking collar 222 down in the opposite axial direction 218. Spring 224 facilitates the needle guard 216 in moving from a retracted position to an extended position and spring 226 facilitates the locking out of the needle guard 216. The action of the springs 224, 226 during operation will be described in more detail below.

The medicated module 200 operates so as to count a dose as being delivered and thereafter to lock-out the needle guard assembly 216 after the dose counted as delivered. Beneficially, the medicated module 200 can lock out after a dose is actually dispensed, and not after a user begins the injection process but does not actually complete dispensing the dose. This is beneficial for a plurality of reasons. For example, such a lock out feature may be beneficial where a user begins the injection process but encounters scar tissue which prevents the user from administering a dose. The components of the medicated module 200 are configured such that the module 200 locks out only after a dose has been delivered, and the configuration of these components is described in greater detail below.

Attachment of the medicated module 200 to drug delivery device 100 is described with reference to FIGS. 4-6 and the operation of the medicated module 200 attached to drug delivery device 100 is described with reference to FIGS. 7-15.

A user may attach the medicated module 200 to the drug delivery device 100 using the attachment means discussed above. The drug delivery device 100 includes a push rod 400. The push rod 400 extends axially along the housing of the device 100 (not explicitly shown). The push rod 400 can protrude from the distal end of the housing. The push rod 400, in particular the distal end section of the push rod 400, is then received in the housing 202 of the medicated module 200 such that mechanical cooperation of the push rod 400 and the sleeve 220 is enabled. The push rod 400, in particular the distal end section of the push rod 400, interacts with sleeve 220. When the drug delivery device 100 is first attached to medicated module 200, the push rod 400 forces the sleeve 220 axially downward in direction 450, moving sleeve 220 closer to locking collar 222. As can be seen in FIG. 4, slanted edge 221 of the sleeve 220 abuts slanted edge 223 of the locking collar 222.

Figure 4:
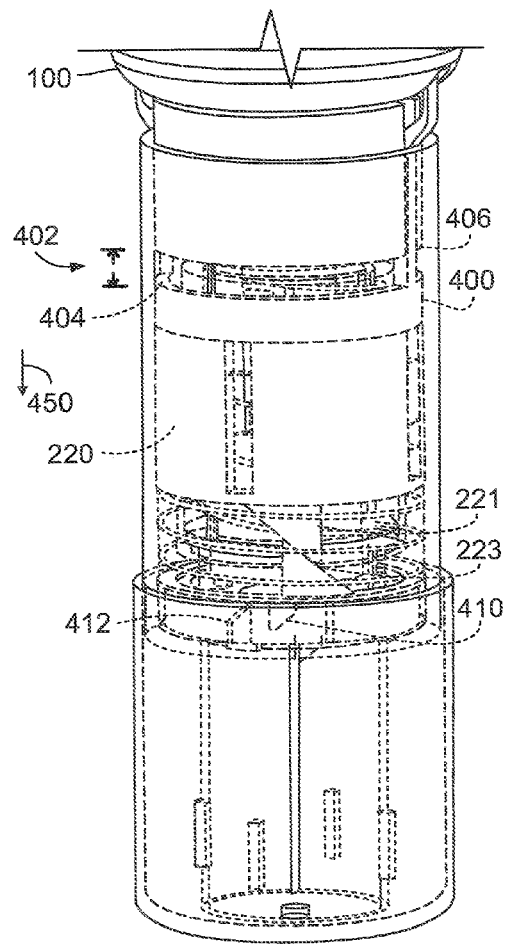
FIG. 4 illustrates the embodiment of FIG. 2 where the medicated module is attached to a drug delivery device.
Figure 7:
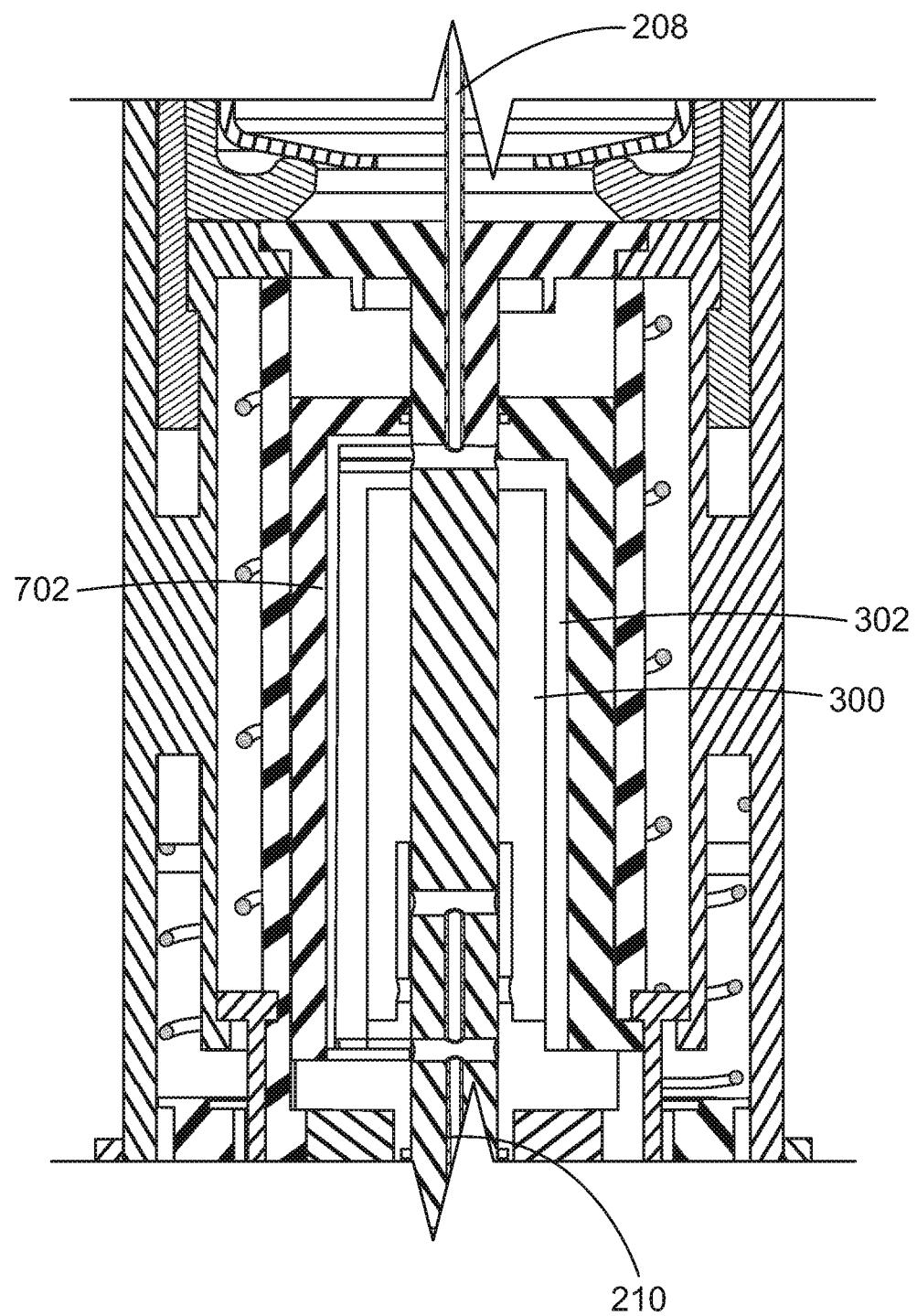
FIG. 7 illustrates a cross-sectional view of the embodiment of FIG. 4 where the needle guard is in an extended position.

Additionally, as seen in FIG. 4, the locking collar 222 includes another slanted feature 410 and the inside of housing 202 includes a slanted feature 412. As will be described in more detail with reference to FIGS. 14-15, slanted features 410 and 412 facilitate the locking-out of the needle guard 216. When attached, slanted feature 410 is, for example, to the right of slanted feature 412. In this position, the needle guard 216 is not locked out and is therefore free to move axially. However, when the device 100 is inserted into the injection site (needle guard 216 retracted), the locking collar 222 is lifted upwards and rotates as slanted feature 221 interacts with the slanted feature on the locking collar 222 and this also consequentially rotates slanted feature 410 to the left and above slanted feature 412. When the needle guard 216 expands after the dose has been dispensed and the needle 210 is removed from the injection site, the locking collar 222 moves downward and slanted feature 410 and 412 interact to begin to lock out the device 100. The locking collar spring 226 then forces the locking collar 222 and needle guard 216 to return to the fully extended position. The force of this spring 226 causes the locking collar 222 to rotate a final amount. It is this final rotation that moves locking feature 416 on the locking collar 222 into axial alignment with locking feature 414 on the needle guard 216. It is this alignment that prevents the needle guard 216 from moving axially. The needle guard 216 and locking collar 222 are now axially engaged and the axial movement of the needle guard 216 is now constrained to that of the locking collar 222. The constraint of movement is such that the needle 210 is substantially covered in the locked out condition therefore preventing needle stick injuries and further use of the needle.

After a user attaches medicated module 200 to drug delivery device 100 and before the user injects a medicated dose, the user may prime the injection device 100 as desired. The optional priming step is described with reference to FIGS. 5-7. The user may use a dose setter 112 of the drug delivery device 100 to prime the device 100. For example, a user may select a small dose of 1-3 units in order to prime the device 100. Prior to an injection, the second medicament 300 is not in fluid communication with either the first needle 208 or the second needle 210. However, the first and second needles 208, 210 are in fluid communication with one another due to a flow path around reservoir 302. During priming, when a user presses a dosing button 113, the first medicament may be forced in the distal direction from a cartridge of the drug delivery device 100, through the first needle 208, around the reservoir 302, and through the output needle 210. The dose button 113 can be any triggering mechanism that causes the dose of the first medicament that was set by the dose setter 112 to move towards the distal end 132 of the device 100. In a preferred embodiment, the dose button 113 is operably connected to a spindle that engages a piston in the primary reservoir of the first medicament.

This path around the reservoir 302 is preferably created by channel 702 located around the reservoir 302. This channel 702 allows for fluid communication between the first needle 208 and second needle 210 when the needle guard 216 is in an extended position.

After priming as desired, a user may administer a dose. It should be understood that when administering a dose, the user will press the medicated module 200 against an injection site, which will retract the needle guard assembly 216, and a user will depress a dosing button 113 in order to deliver the dose. The components of the medicated module 200 (and specifically the sleeve 220 and locking collar 222) are configured to perform different mechanical operations depending on whether the user (i) only retracts the needle guard 216 or (ii) retracts the needle guard 216 and depresses the dosing button 113.

For clarity, the operation of the medicated module 200 with the needle guard 216 retracted and without the dose dispensed is described followed by the operation of the medicated module 200 with the needle guard 216 retracted and with the dose dispensed. It should be noted that the operation of the module 200 is not necessarily performed in connection with the delivery of a dose to a user. No interaction of the medicated module 200 with the human or animal body needs to take place. In particular, operation of the medicated module 200 may take place for testing the functionality of the module 200, for example.

In most instances, a user will depress the needle guard 216 and fully depress the dosing button 113 when administering a dose. However, in some instances, a user may retract the needle guard 216 without fully depressing the dosing button 113. In such a case, the medicated module 200 does not count a dose as being delivered, and therefore does not subsequently lock the device 100 out.

Figure 8:
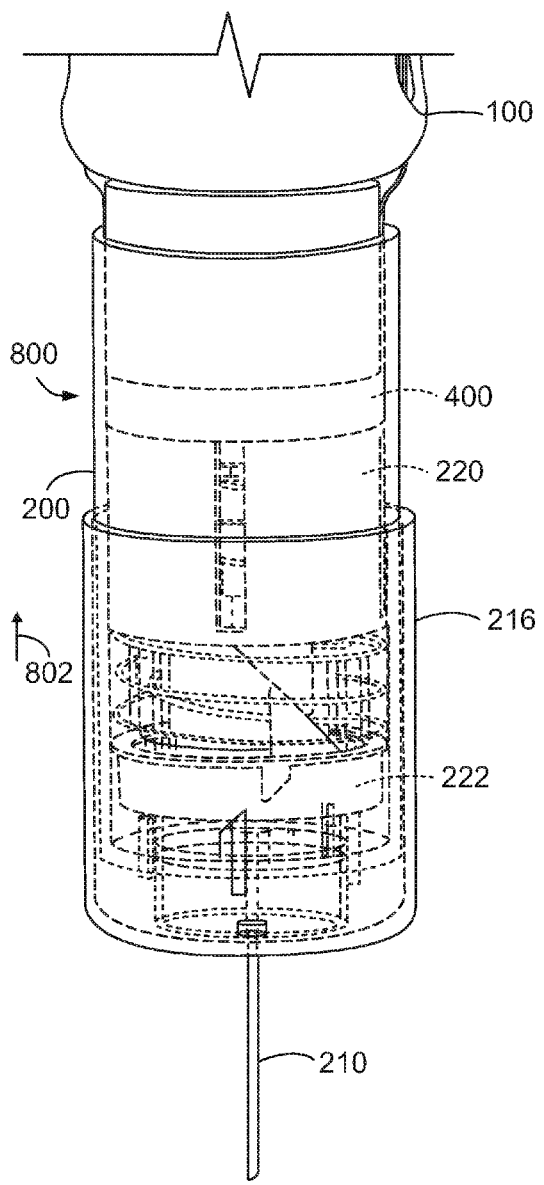
FIG. 8 illustrates a perspective view of the embodiment of FIG. 4 where the needle guard is in a retracted position.

FIG. 8 illustrates a perspective view of the embodiment of FIG. 4 where the needle guard 216 is in a retracted position. In this view, the dosing button 113 is not depressed. As can been seen, when the needle guard assembly 216 is refracted in axial direction 802, second needle 210 is no longer guarded. Preferably, the needle guard 216 is retracted as a user applies the module 200 to an injection site, and the second needle 210 would therefore pierce the injection site to allow for subcutaneous injection. It is also clear that retracting the needle guard 216 also moves the locking collar 222 and the sleeve 220 axially in direction 802. As the user dials the dose selector out of the housing of the primary device 100, the push rod 400 (being acted upon by the spring) 'pops' out. As can be seen, this movement removes the gap 402 between points 404 and 406 (compare FIG. 4), as evidenced by point 800. At this point when the needle guard 216 is retracted but a dose button 113 is not yet fully depressed, the medicated module 200 has not yet counted a dose. A user could allow the needle guard 216 to return to an extended position, and the medicated module 200 components will return to as shown in FIG. 4. When the needle guard 216 is retracted and the dose button 113 not depressed, the locking collar 222 is not rotated far enough to move into the locking state and consequently the mechanism returns to its unlocked starting position until used again.

Figure 9:
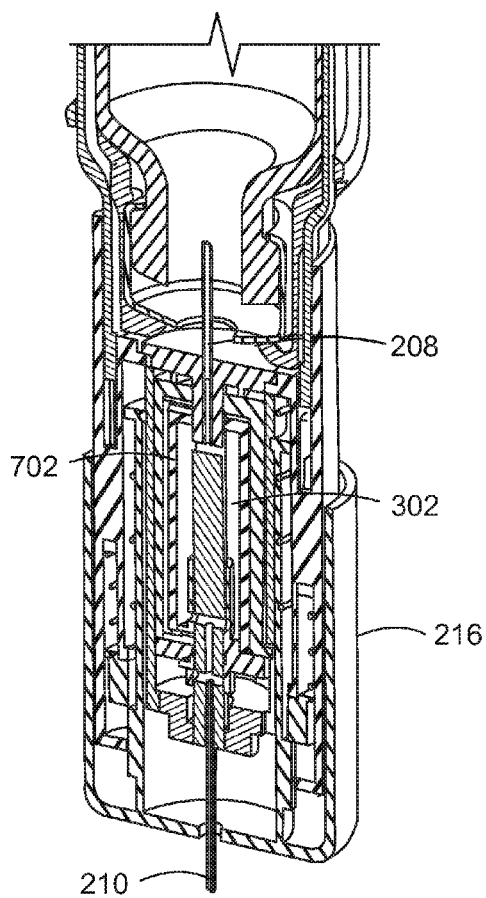
FIG. 9 illustrates a perspective, cross-sectional view of the embodiment of FIG. 4 where the needle guard is in a retracted position.
Figure 10:
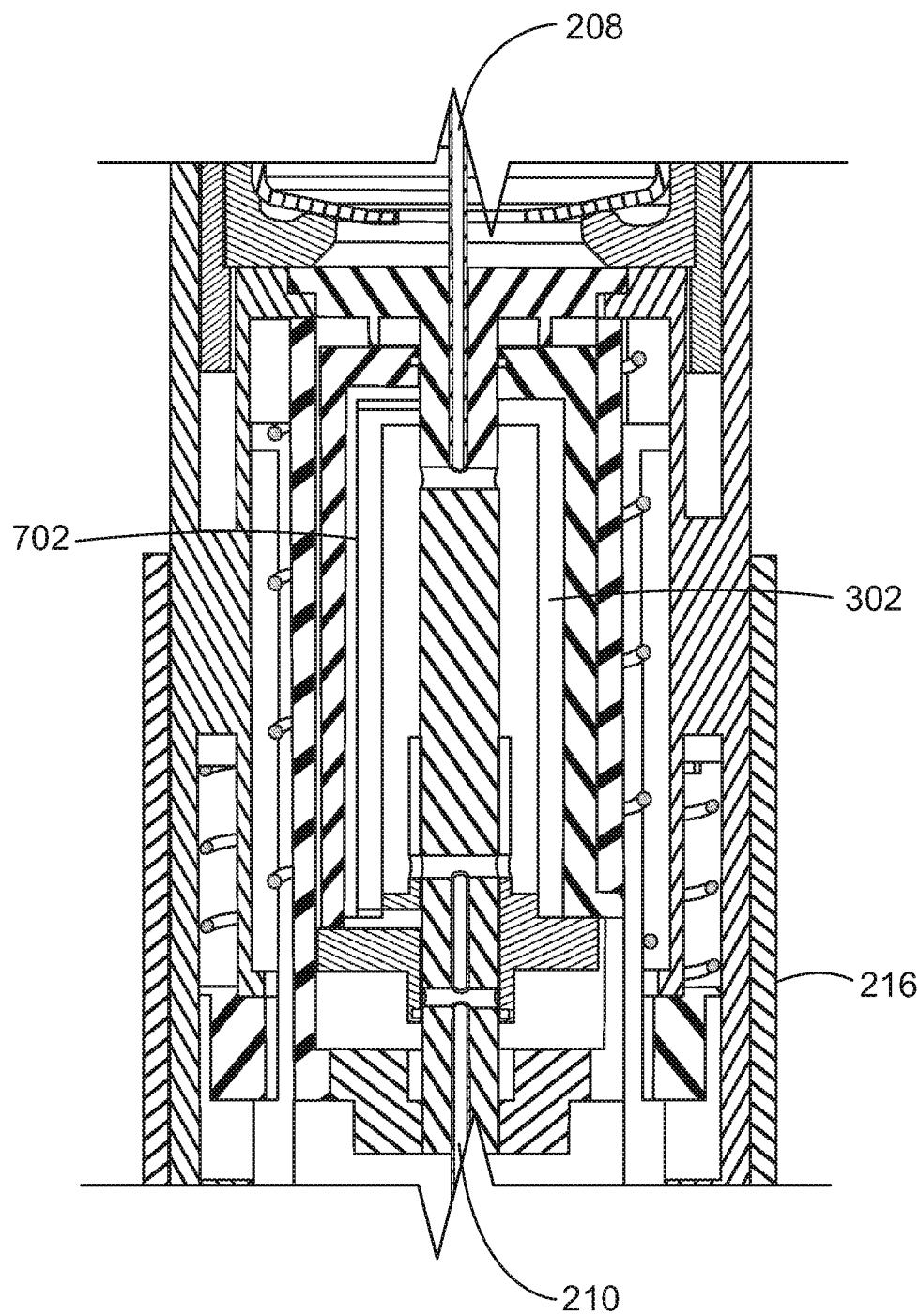
FIG. 10 illustrates a cross-sectional view of the embodiment of FIG. 4 where the needle guard is in a retracted position.

FIG. 9 illustrates a perspective, cross-sectional view of an embodiment where the needle guard 216 is in a retracted position and FIG. 10 illustrates a close-up view of the reservoir 302. As can be seen in FIG. 10, the movement of the needle guard 216 forces the needle 208 to pierce the reservoir 302. Therefore, the needles 208, 210 are in fluid communication with the reservoir 302. Further, as seen in FIG. 10, needles 208 and 210 are no longer in fluid communication with bypass channel 702.

Figure 11:
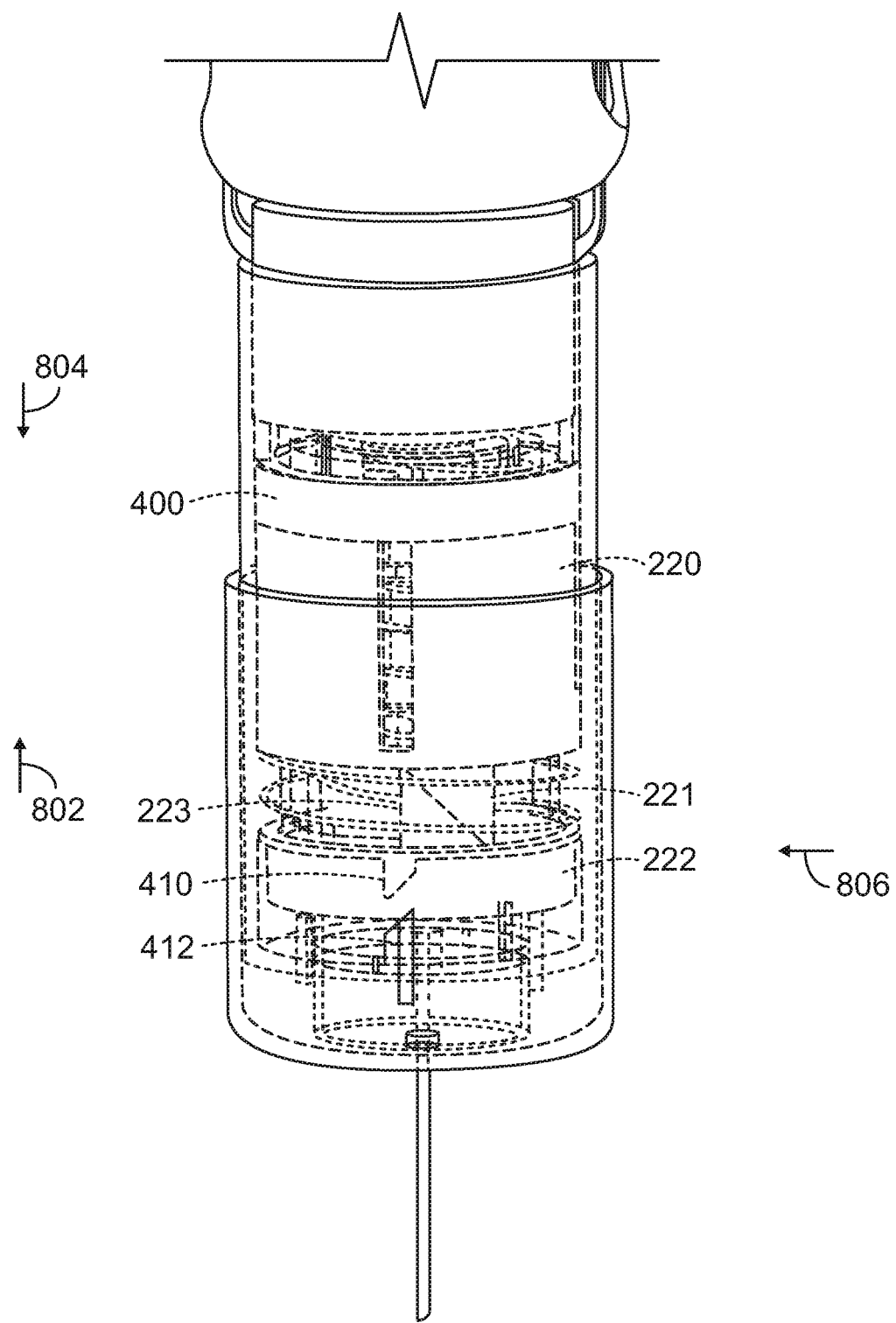
FIG. 11 illustrates a perspective view of the embodiment of FIG. 4 where the needle guard is in a retracted position and the push rod is depressed.

FIG. 11 illustrates a perspective view of the embodiment where the needle guard 216 is in a refracted position and the push rod 400 is depressed. This counts the dose and consequently allows the medicated module 200 to lock out because both the needle guard 216 has moved in a proximal direction and a dose has been delivered (the dose button 113 fully depressed). This occurs through the interaction of (i) the push rod 400 with the sleeve 220 and (ii) the locking collar 222 and the sleeve 220. As mentioned above, during dosing, a user retracts the needle guard 216 in a first axial direction 802. This retraction forces the locking collar 222 and the sleeve 220 to move axially in the direction 802. As a user depresses the dosing button 113, at the end of depressing the dose button 113, the dose button 113 pushes the push rod down in a second axial direction 804. The second direction 804 is substantially opposite the first direction 802. The push rod 400 pushes sleeve 220 in direction 804.

As sleeve 220 is pushed in direction 804, the sleeve 220 interacts with the locking collar 222 and forces the locking collar 222 to rotate in direction 806 (the locking collar 222 is constrained axially on features attached to the needle guard 216). This is accomplished due to the interaction of slanted features 221 and 223. As depicted, the slanted features 221, 223 may have a slant of approximately 45 degrees. However, it should be understood that the slanted features 221, 223 may have slants of different angles, so long as the at least two features may interact and force the locking collar 222 to rotate. For example, slanted feature 221 may have a slant of 30 degrees and slanted feature 223 may have a slant of 60 degrees. Other angles are possible as well. It is this combined axial movement from the push rod 400 and needle guard 216 retraction and the subsequent rotational movement of the locking collar 222 that counts a dose as delivered, because the dose button 113 needs to be depressed and the needle guard 216 needs to be retracted for the locking collar 222 to move axially up and then be rotated far enough to begin to engage the locking mechanism.

Figures 12, 13:
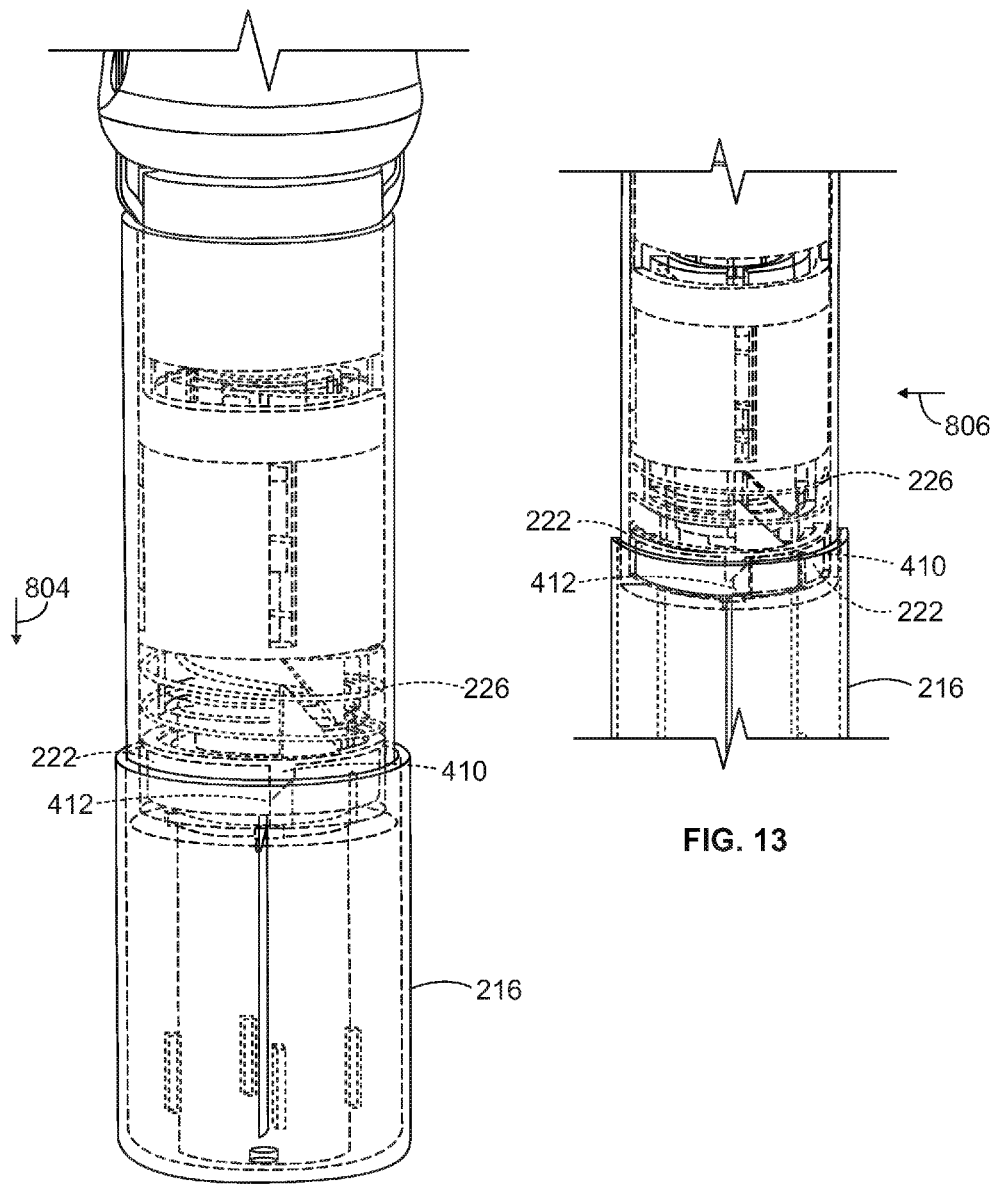
FIG. 12 is a perspective view of the embodiment of FIG. 4 just prior to where the needle guard is locked out.
FIG. 13 is a perspective view of the embodiment of FIG. 4 where the needle guard is locked out.

After counting this dose as delivered, the components of the medicated module 200 are designed to lock out the needle guard 216 after it returns to an extended position. FIG. 12 is a perspective view of the medicated module 200 just prior to the medicated module 200 is locked out and FIG. 13 is a perspective view of the embodiment of FIG. 4 where the needle guard 216 is locked out.

Specifically, as needle guard 216 extends under the force of spring 224, locking collar 222 moves axially in direction 804 under the force of spring 226. Due to the fact that locking collar 222 rotated as the dose was counted by the device 100, slanted feature 410 is located above slanted feature 412. As seen in FIG. 12, these slanted features 410, 412 abut one another, and as seen by FIG. 13, slanted feature 412 causes locking collar 222 to rotate circumferentially in direction 806. It is this final rotational movement that engages locking collar 222 with a locking feature 414 on the needle guard 216.

Figure 14:
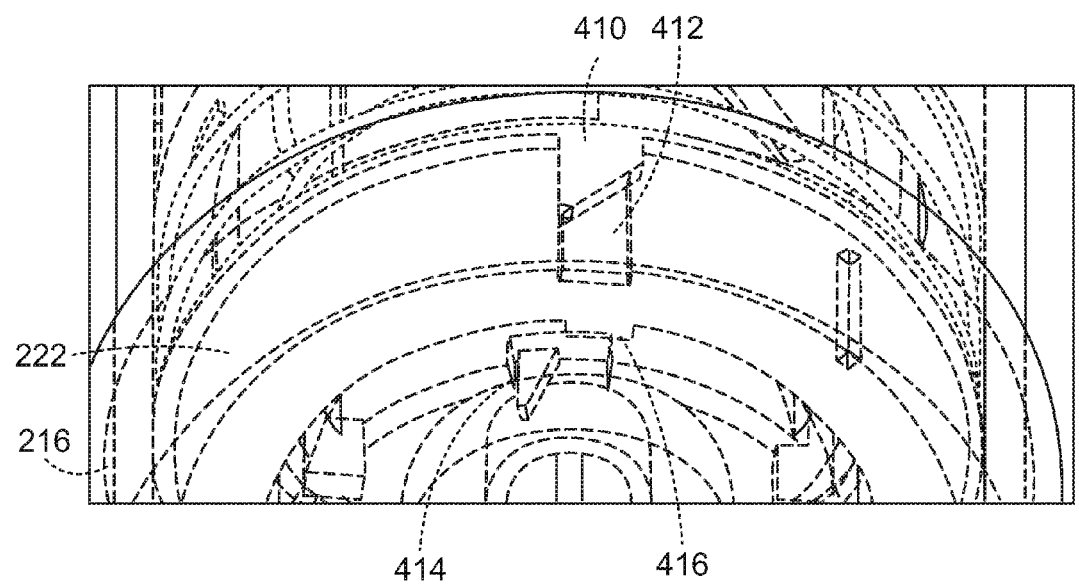
FIGS. 14-15 are perspective views of the medicated module that show the needle guard locking out.
Figure 15:
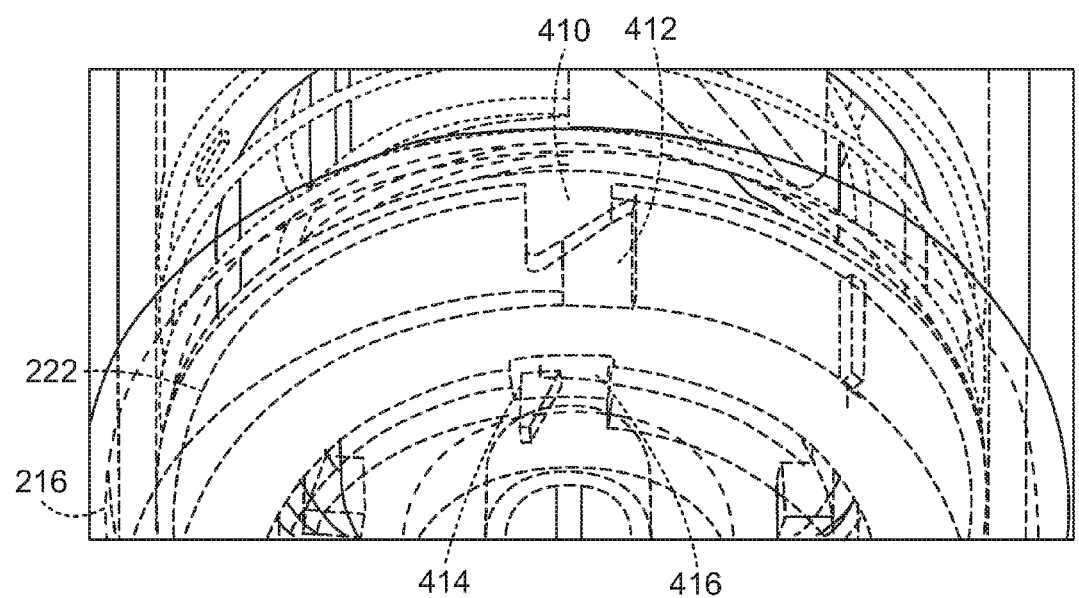

FIGS. 14-15 are detailed perspective views of the locking collar 222 and a proximal end of needle guard 216 that show the locking collar 222 and needle guard 216 when the needle guard 216 is locking out, in accordance with an embodiment of the present disclosure. FIG. 14 shows the locking collar 222 and needle guard 216 when needle guard 216 in an extended position but just before the locking collar 222 rotates to lock the needle guard 216 in place. FIG. 15 shows the same features but with the locking collar 222 rotated into the locked position, as locking feature 416 locks into locking feature 414. Locking feature 416 is preferably a protrusion from locking collar 222. This protrusion may be rectangular shaped, as depicted in FIGS. 14-15. However, other shapes are possible as well. Locking feature 414 preferably comprises a recess that locking feature 416 may fall into.

The slanted feature 412 on the needle guard 216 helps facilitate the lock out. The needle guard 216 is rotationally constrained, but axially free to move. As mentioned above, during use the needle guard 216 is free to move axially. As described above with reference to FIG. 4, the needle guard 216 retracts during insertion of the needle 210, the locking collar 222 partially rotates due to the action of the slanted feature 221 acting on the slanted edge of feature 223 of the locking collar 222. On release of the needle guard 216 (i.e., as the needle guard 216 extends back to its rest extended state) it moves axially. At the same time, the locking collar 222 moves axially. When the needle guard 216 is in the fully extended position, the locking collar 222 starts to abut feature 412 under the force of its axial compression spring. Under the action of the spring 226, the locking collar 222 acts on a slanted feature of feature 412 on the needle guard 216 (now in its most extended position). This action causes the locking collar 222 to rotate a final amount.

This final rotation when the needle guard 216 is fully extended causes a feature 416 on the locking collar 222 to rotate into a position such that it blocks the travel of the triangle-shaped locking feature 414 on the needle guard 216. This blocking prevents any further axially movement of the needle guard 216.

In an embodiment, these mating features 414, 416 may be repeated two or more times around the diameter of the device 100, which beneficially provides added stability.

The medicated module has been described above as a single use device that locks out after one injection. However, it should be understood that a medicated module in accordance with embodiments could be designed as a multiple use module that locks out after multiple injections. For instance, the medicated module could be designed to count three doses as delivered and lock out after the third dose is delivered. Generally, the system may be designed to count any predefined number of doses, such as a number of doses between two doses and four doses. As mentioned above, to allow predefined multiple doses before lock out, the sleeve and/or locking collar may have additional teeth designed to gradually rotate the locking collar a known distance each time the needle guard retracted and extended. After a defined number of increments (the required dose count) the needle guard would then lock in the extended position.

In any of the above described embodiments, the second medicament in the medicated module may be either in a powdered solid state, any fluid state contained within the reservoir, or coated to the inside surface of the drug dispense interface. The greater concentration of the solid form of the medicament has the benefit of occupying a smaller volume than the liquid having lower concentration. This in turn reduces the ullage of the medicated module. An additional benefit is that the solid form of the second medicament is potentially more straightforward to seal in the secondary reservoir than a liquid form of the medicament. The device would be used in the same manner as the preferred embodiment with the second medicament being dissolved by the first medicament during dispense.

The connection or attachment between the medicated module of the above described embodiments may contain additional features (not shown), such as connectors, stops, splines, ribs, grooves, and the like design features, that ensure that specific medicated module are attachable only to matching drug delivery devices. Such additional features would prevent the insertion of a non-appropriate medicated module to a non-matching injection device.

The shape of the medicated module may be a cylindrical body or any other geometric shape suitable for defining a fluid reservoir or for containing a discrete self-contained reservoir of the secondary medicament and for attaching one or more needle cannula. The medicated module can be manufactured from glass or other drug contact suitable material. The integrated injection needle can be any needle cannula suitable for subcutaneous or intramuscular injection. Preferably the medicated module is provided by a drug manufacturer as a stand-alone and separate device that is sealed to preserve sterility. The sterile seal of the module is preferably designed to be opened automatically, e.g. by cutting, tearing or peeling, when the medicated module is advanced or attached to the drug delivery device by the user.

The medicated module of the present disclosure could be designed to operate in conjunction with a multiple use injection device, preferably a pen-type multi-dose injection device, similar to what is illustrated in FIG. 1. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose and preferably a multi-dose device, however, in some cases it may be beneficial to use a single dose, disposable device.

A typical injection device contains a cartridge or other reservoir of medication. This cartridge is typically cylindrical in shape and is usually manufactured in glass. The cartridge may be sealed at one end with a rubber bung and at the other end by a rubber septum. The injection device may be designed to deliver multiple injections. The injection device may further comprise a dose setter; the dose setter may be operably connected to the reservoir. The injection device may comprise a dose button; the dose button may be operably connected to the reservoir. The dose button may be any triggering mechanism that causes the dose of the medicament that was set by the dose setter to move distally towards the distal end of the device. In a preferred embodiment, the dose button is operably connected to a spindle that engages a piston in the reservoir. In a further embodiment the spindle is a rotatable piston rod comprising two distinct threads. The delivery mechanism is typically powered by a manual action of the user, however, the injection mechanism may also be powered by other means such as a spring, compressed gas or electrical energy.

Exemplary embodiments of the present invention have been described. Those skilled in the art will understand, however, that changes and modifications may be made to these embodiments without departing from the true scope and spirit of the present invention, which is defined by the claims.

We claim:

1. A medicated module attachable to a drug delivery device, wherein the drug delivery device comprises a primary reservoir for retaining a first medicament and wherein the medicated module comprises a second medicament, the medicated module further comprising:
   a reservoir for retaining the second medicament;
   a proximal needle cannula and a distal needle cannula, wherein the reservoir is arranged in the axial direction between the proximal needle cannula and the distal needle cannula, wherein the distal end of the distal needle cannula is configured to be applied to an injection site and wherein the proximal end of the proximal needle cannula is configured for piecing the primary reservoir;
   a needle guard to provide protection against the distal needle cannula arranged in a portion of the medicated module and configured to move in an axial direction during application to an injection site;
   locking means for disabling axial movement of the needle guard, wherein the locking means include a rotating member and a module coupling member, the locking means being configured to be operably connected to an activation of a dose button of the drug delivery device and to an axial movement of the needle guard;
   wherein the locking means are further configured to disable the needle guard from moving axially only after a predefined number of dose delivery operations, wherein a dose delivery operation comprises the steps of moving the needle guard in axial direction and activating the dose button for delivering a dose.

2. The medicated module of claim 1, wherein the locking means is configured such that only an activation of the dose button in a retracted position of the needle guard is counted as a dose delivery operation.

3. The medicated module of claim 1 configured such that the needle guard is axially movable until the predefined number of dose delivery operations have been carried out.

4. The medicated module of claim 1, wherein the rotating member is configured such that the rotating member carries out a defined rotational movement after each dose delivery operation, thereby counting the number of delivered doses.

5. The medicated module of claim 4, wherein the needle guard comprises a locking feature for disabling axial movement of the needle guard, and wherein the locking means is configured such that the rotating member engages with the locking feature after the predefined number of doses is delivered.

6. The medicated module of claim 4, further comprising a first spring and a second spring, wherein the first spring is operably connected to the needle guard and the second spring is operably connected to the rotating member.

7. The medicated module of claim 6, wherein after a given dose is delivered, the first spring forces the needle guard in an axial direction, and the second spring forces the rotating member in the axial direction so as to facilitate counting the given dose as delivered.

8. The medicated module of claim 1, wherein the module coupling member is engagable with a device coupling member of the drug delivery device, wherein the device coupling member is operably connected to the dose button, and wherein the module coupling member is configured to be axially movable.

9. The medicated module of claim 8, wherein the module coupling member comprises a first slanted feature, wherein the rotating member comprises a second slanted feature, and wherein, when a given dose is delivered, the first slanted feature and second slanted feature interact to force the rotating member to rotate, so as to facilitate counting the given dose as delivered.

10. The medicated module of claim 1, wherein the predefined number of doses is in a range from one dose to four doses.

11. The medicated module of claim 1, having at least one of the following designs:
  a) the module coupling member comprises a sleeve;
  b) the rotating member comprises a locking collar; or
  c) a device coupling member comprises a push rod.

12. The medicated module of claim 1, where the proximal needle cannula is mounted in a proximal end of the medicated module and the distal needle cannula is mounted in a distal end of the medicated module, wherein the two needle cannula are in fluid communication with the second medicament when the needle guard is retracted in a proximal direction.

13. A drug delivery system to deliver two or more medicaments comprising a medicated module of claim 1 and further comprising:
  a dose button operably connected to the locking means of the medicated module;
  a device coupling member operably connecting the dose button to the locking means; and
  a primary reservoir of medicament containing at least one drug agent, where the medicated module is configured for fluid communication with the primary reservoir.

14. The drug delivery system of claim 13, wherein during delivery of a given dose:
  (i) the given dose is selected, upon which the device coupling member and the module coupling member move in a first axial direction,
  (ii) the needle guard is retracted in the first axial direction, thereby forcing the rotating member to move axially in the first direction,
  (iii) the device coupling member thereafter moves in a second axial direction and forces the module coupling member to move in the second axial direction, wherein the second axial direction is substantially opposite the first axial direction, and
  (iv) the module coupling member interacts with the rotating member and forces the rotating member to rotate circumferentially,
  (v) as the needle guard extends in a second axial direction substantially opposite to the first axial direction, it allows the rotating member to move axially in the second direction and rotate circumferentially, so as to count the given dose as delivered.

15. A method for testing a drug delivery system, comprising the steps of:
  A) providing a medicated module according to claim 1;
  B) attaching the medicated module to a drug delivery device, wherein the drug delivery device comprises a dose button, a primary reservoir of medicament, and a device coupling member operably connected to the dose button;
  C) setting a dose of medicament on the drug delivery device such that the device coupling member is moved proximally;
  D) activating the dose button to perform a priming operation such that the medicament is forced in the distal direction from the primary reservoir of the drug delivery device around the reservoir of the medicated module, and through the needle.

16. The method of claim 15, further comprising the steps of:
  E) moving the needle guard in the proximal direction, thereby moving the module coupling member in the proximal direction by mechanical cooperation of the needle guard and the module coupling member;
  F) setting a further dose of medicament on the drug delivery device such that the device coupling member is moved proximally;
  G) activating the dose button to move the device coupling member distally, thereby moving the module coupling member distally and activating the rotating member disposed in the medicated module by mechanical cooperation of the module coupling member and the rotating member, wherein the activation of the rotating member is configured to prevent the needle guard in the medicated module from moving axially by mechanical cooperation of the rotating member and the needle guard after a predefined number of doses was delivered.

* * * * *